United States Patent [19]

Lee et al.

[11] Patent Number: 5,508,041

[45] Date of Patent: Apr. 16, 1996

[54] MICROENCAPSULATION FOR CONTROLLED ORAL DRUG DELIVERY SYSTEM

[75] Inventors: Haibang Lee; Soonhong Yuk, both of Daejun, Rep. of Korea

[73] Assignee: Korea Research Institute of Chemical Technology, Rep. of Korea

[21] Appl. No.: 285,024

[22] Filed: Aug. 2, 1994

Related U.S. Application Data

[62] Division of Ser. No. 775,698, Oct. 10, 1991, Pat. No. 5,362,424.

[30] Foreign Application Priority Data

Oct. 11, 1990 [KR] Rep. of Korea ............... 90-16120
Feb. 7, 1991 [KR] Rep. of Korea ............... 91-2092

[51] Int. Cl.$^6$ .................................................. A61K 9/50
[52] U.S. Cl. ........................... 424/451; 424/455; 424/456; 424/489; 514/779; 514/781; 514/782; 514/783; 514/784; 514/788; 514/938; 514/951
[58] Field of Search ..................... 424/455, 6, 489, 424/493, 494, 496, 497, 451

[56] References Cited

U.S. PATENT DOCUMENTS 3,749,799  7/1973  Cort et al. .................... 424/344
3,819,838  6/1974  Smith et al. .................. 426/89

FOREIGN PATENT DOCUMENTS 2086835  5/1982  United Kingdom.

Primary Examiner—Thurman K. Page
Assistant Examiner—James M. Spear

[57] ABSTRACT

The invention relates to a microencapsulated emulsion a drug-dispersed oil core surrounded by a water-insoluble capsule material. The capsule material is made up of a polysaccharide which has metal chelating capacity, a biocompatible and water-soluble polymer for improving the physical properties of the capsule material, and emulsifying agents. The ratio of polysaccharide to polymer in the capsule material is at least capsule material, and emulsifying agents. The ratio of polysaccharide to polymer in the capsule material is at least 0.25.

14 Claims, 1 Drawing Sheet

5,508,041

MICROENCAPSULATION FOR CONTROLLED ORAL DRUG DELIVERY SYSTEM

This is a divisional of application Ser. No. 07/775,698, U.S. Pat. No. 5,362,424 filed Oct. 10, 1991.

BACKGROUND OF THE INVENTION

1. Field of the Invention

This invention relates to a microencapsulated emulsion for a controlled oral drug delivery system. In particular, it relates to a microencapsulation of oil droplets containing a drug for oral administration.

In particular, it relates to a method for microencapsulation of a drug for oral administration using biodegradable and biocompatible materials such as polysaccharide that have a metal chelating capacity for the purpose of minimizing gastric upset or damage to the stomach.

More particularly, it relates to a microencapsulation of oil-containing drugs for oral administration using a biodegradable and biocompatible material such as polysaccharide for the purposes of minimizing the degradation of the drug caused by hepatic first-pass metabolism by inducing lymphatic absorption of the drug, and the degradation of the drug in the strong acidic condition of gastric juice.

Recently, research groups have focused their studies on a desirable drug carrier system because the existing methods for medicating drugs by oral administration or injection suffer from many problems witch regard to 1) the degradation of the drug by hepatic first-pass metabolism, 2) the severe gastric upset or damage to the stomach by the drug's activity, 3) the degradation of the drug in the stomach by the strong acidic condition of gastric juice.

However, the existing methods for drug administration using oral route or injection continue to be used because of their convenience.

Although in principle the entire gastrointestinal tract is capable of drug absorption, the small intestine is the major site of absorption for the drug. A drug molecule, after diffusing through the mucosa of the intestine, is accessible to both lymphatic and blood circulation. If a drug is administered via the oral route, it must pass through the gut wall and then through the liver before reaching the systemic circulation and its site of action. Extensive hepatic first-pass metabolism in the liver is often encountered, and a fraction of the dose administered may be eliminated before reaching the systemic circulation.

Accordingly, an increased amount of drug dose and dosing frequency are required to maintain blood levels within the therapeutic range. This results in severe gastric upset or damage to the stomach.

Furthermore, for a cancer patient, the anticancer drugs given orally cause adverse effects because most antitumor agents are not selective, but are highly toxic for both cancer and normal cells.

In lymphatic absorption, drug molecules enter directly into systemic circulation by bypassing the liver. Thus, the overall blood levels of drugs which undergo significant metabolism in the liver can be significantly increased if they can be directed to the lymphatic fluid.

In general, the lymphatic system is not an important route for drug entry into the body except for highly lipophilic compounds, such as dietary fat, cholesterol, and lipid soluble vitamins.

In the present invention, in order to use the advantages of the lymphatic system as a drug absorption route, the inventors attempted to use an emulsion as drug carrier systems to transport medical drugs. The oil emulsions are absorbed easily into lymphatic capillaries and transported to regional lymph nodes. As a result, the oil emulsion can be considered as a drug carrier to the lymphatic system by oral administration as well as by injection into tissues.

Accordingly, an emulsion containing anticancer agent is available in chemotherapeutic drug dosage form for lymph node metastasis, which is most common in human cancer.

In the case of oral administration of an emulsion containing an anticancer drug, most anticancer drugs are released in the stomach. Therefore, anticancer agents can not react in the small intestine. Thus, in the case of oral administration, the chemotherapeutic effect of anticancer drugs is limited only to stomach cancer. (CRC: Critical Review in Therapeutic Drug Carrier Systems, vol. 2 No. 3, pp. 245, 1986)

2. Description of the Prior Art

As to the conventional method for microencapsulating liquid fatty material such as by oil emulsion, U.S. Pat. Nos. 3,008,083; 3,749,799; and 3,819,838 disclose a solidification method of the capsule material, gelatin, by rapidly lowering the temperature and subsequent dehydration. While methods such as those disclosed in the patent literature set forth above have achieved some significant commercial success, difficulties have sometimes been encountered in rapidly inducing solidification of the microencapsulating material.

British Pat. No. 2,086,835 provides a process for encapsulating oils using polysaccharide as a material for bead matrix. However, this method produces shape-retaining, substantially water insoluble micro-beads containing thousands of oil droplets in the bead matrix. This process can not provide a microencapsulated emulsion which is individually microencapsulated oil droplets in the powdery state having a diameter of less than 5μm.

Japan Patent No. 59-228930 provides a process for encapsulating olive oil using sodium alginate as capsule material. In this method, the core and capsule materials flow down as double layers on a vertical cone vibrated supersonically and the microcapsules are received in hardening solution or dried to harden the capsule material. This method requires a very complex apparatus for microencapsulation.

SUMMARY OF THE INVENTION

This invention provides a microencapsulation of oil droplets containing drugs for oral administration. The microencapsulated emulsion obtained in this invention represses the drug release from the emulsion and protects the emulsion and drug from the strong acidic condition of gastric juice. The oil droplets and drugs dispersed in the oil droplets are released rapidly in the small intestine with the disintegration of capsule material.

That is, the present invention provides a drug carrier system for oral administration which improves the prior system using biodegradable and biocompatible natural polymer such as polysaccharide having a metal chelating capacity.

This present invention specifically provides a method for microencapsulation of oil droplets containing a drug for oral administration. The microencapsulated emulsion obtained in this invention can reduce the gastric upset or damage to the stomach and can minimize the degradation of the drug caused by hepatic first pass metabolism, by inducing lymphatic absorption.

First of all, the drug is mixed with liquid oil by sonication for 5–30 seconds to disperse the drug homogeneously in the oil phase., The drug-dispersed oil phase to be incorporated into the microcapsule is added to an aqueous solution mixture (to be used as capsule material) of polysaccharide which has metal chelating capacity, biocompatible and water soluble polymer (to improve the physical property of capsule material), and emulsifying agents. The two phase system (oil/aqueous solution mixture) is subjected to sonication to produce an oil-in-water emulsion containing the drug-dispersed oil droplets in the 1–5μm range of diameter.

As soon as possible after formation of the emulsion, the emulsion is added to a multivalent cation-containing solution to harden the capsule material. Finally, the microencapsulated emulsion is freeze-dried to obtain a final product in powdery state.

The polysaccharide having metal chelating capacity includes sodium alginate, pectin, xanthomonas campestris (XCPS), and carboxymethylcellulose ( CMC).

The alginic acid family of linear 1–4 linked glycuronans are the copolymers composed of β-D-mannopyranuronic acid (M) residue and α-L-gulupyranuronic acid (G) residues that are arranged in homopolymeric (GG and MM) and heteropolymeric (MG) sequences in varying proportions and distribution patterns. Alginic acid can be derived from algal or bacterial sources.

In the present invention, sodium salt of alginic acid was used as microcapsule material. Sodium alginate is water-soluble and has good biodegradability, and sodium alginate is widely used for food, cosmetics, medicine, and pharmaceuticals, because it is a biodegradable and biocompatible material without immunogenic effect.

The biocompatible polymers used as capsule material mixed with polysaccharide in this invention include polyamino acid, sodium salt of polyacrylic acid, polylatic acid hydroxypropyl methylcellulose, and collagen protein. These polymers are available in markets and are used for cosmetics, toothpaste, shampoo, painting, and adhesives. These polymers are water soluble and mix with polysaccharide in aqueous solution homogeneously.

The desirable mixing ratio of polysaccharide and these polymers is from 100:0 to 20:80. If the content of the polymer exceeds 80 wt % of solution mixture, the hardened capsule material can not be obtained.

The core material in the invention is a liquid oil which is used widely for food or pharmaceuticals. Some representative examples of such liquid oil include corn oil, peanut oil, coconut oil, castor oil, sesame oil, soy bean oil, perilla oil, sunflower oil, and walnut oil.

Any type of drug which is stable upon being subjected to sonication can be incorporated with the oil phase in this invention. For example, these drugs include steroid drugs, anticancer drugs like 5-flourouracil and Me-CCNN, antibiotic, and antiulcer drugs like Omeprazole. The drug is incorporated into the oil phase in this invention in an amount of 1–40 wt % of the liquid oil. If the amount of the drug is more than 40 wt %, the excess drug may beextracted from the liquid oil.

In this invention, the emulsifying agents are used in the process in order to prepare for the stable oil-in-water emulsion. These emulsifying agents should be nontoxic and nonimmunogenic substances. Some examples of emulsifying agents in the invention include Tween 20, Tween 40, Tween 80, bile salt, sodium cholate, a mixture of 80 wt % ethyleneglycol 1000 monocetylether and 20 wt % ethyleneglycol 400, and polyoxyethylenether. The amount of emulsifying agents used in this invention is 5–10 wt % of the total amount of case and capsule material. If the amount of emulsifying agents is less than 0.5 wt %, the emulsion can not be formed.

The amount of aqueous phase of capsule material is 100–200 wt % of the total amount of liquid oil and drug.

Multivalent cations used in this invention may include aluminum ($Al^{+3}$) ions, calcium ($Ca^{+2}$) ions, or magnesium ($Mg^{+2}$) ions in a concentration of 0.5–5 wt %.

In this present invention, the inventors use emulsification, chelation, and freeze-drying for the preparation of a microencapsulated emulsion containing drugs for oral administration, instead of rapid temperature reduction and dehydration as disclosed in the prior art.

While the invention disclosed in British Pat. No. 2,086,835 provides multiply compartmentalized micro-beads, and the invention disclosed in Japan Pat. No. 59-288930 provides diversified microcapsules with a diameter of 20–100 μm using the special apparatus for sonication, it is the advantage of the present invention that the powdery microencapsulated emulsions with regular size can be obtained and that no special equipment for microencapsulation is required.

DESCRIPTION OF THE PREFERRED EMBODIMENT

Figure 1:
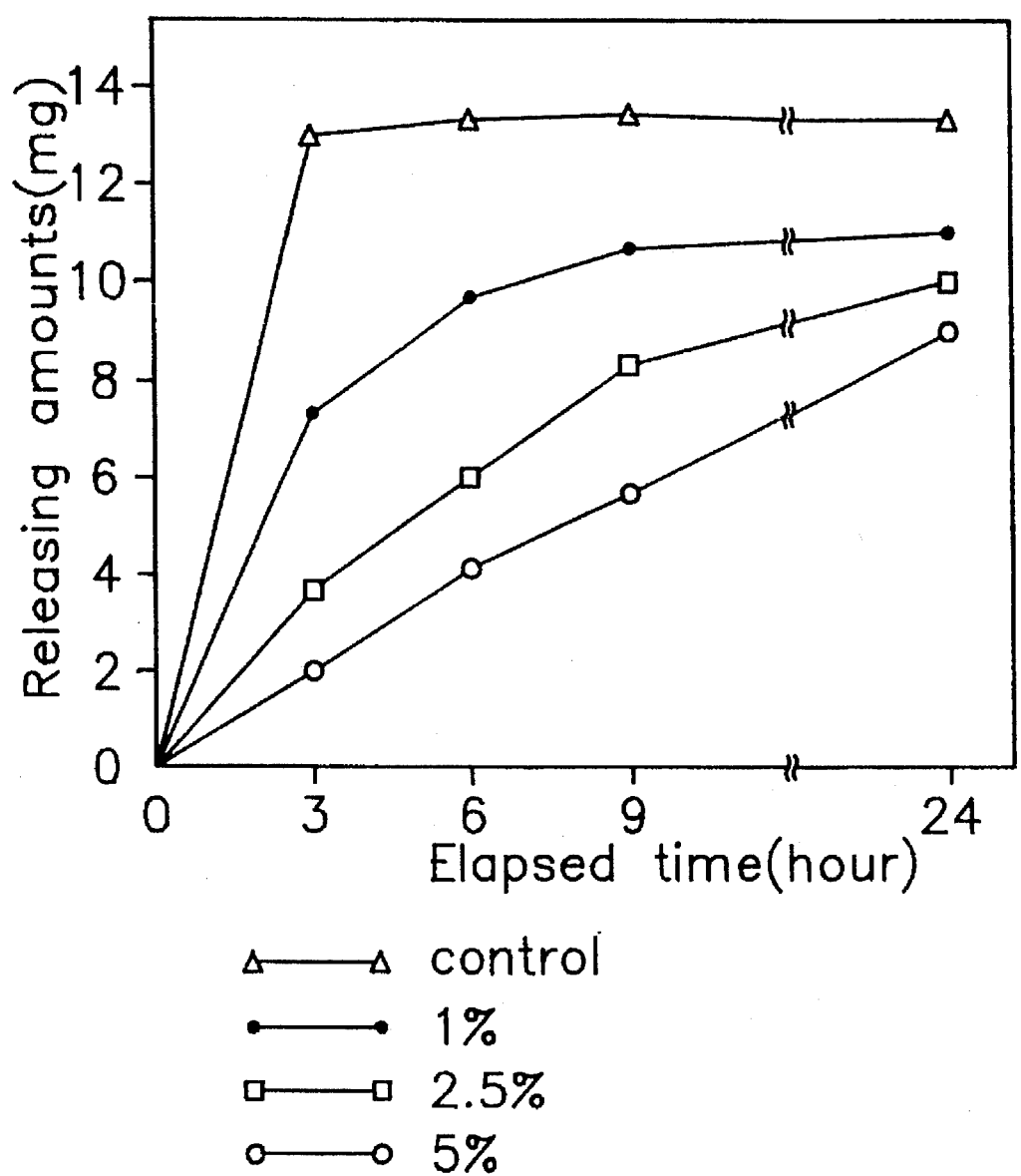
FIG. 1 is a graph showing amount of drug released as a function of time.

The invention will now be further understood from the following non-limiting examples, wherein all percentages are given by weight.

EXAMPLES

Example 1

4 parts of 5-fluorouracil (anticancer drug) as a model drug was mixed with 20 parts of corn oil as a core material by sonication for 10 seconds to disperse the drug homogeneously in the oil phase.

The drug-dispersed oil phase to be incorporated into the microcapsule was added to 20 parts of the aqueous solution of 5% sodium alginate (Junsei Chemical Co., Ltd. Japan) containing 2.5 parts of bile salt as an emulsifying agent (Sigma Co., Ltd. U.S.). The two phase system (oil/aqueous solution mixture) was subjected to sonication to produce oil-in-water emulsion containing the drug-dispersed oil droplets in the 1–5 μm range of diameter. As soon as possible after formation of the emulsion, the emulsion was added to 100 parts of 2.5% aluminum sulfate [$Al_2(SO_4)_3$] aqueous solution to harden the capsule material (sodium alginate).

Finally, the microencapsulated emulsion is freeze-dried to obtain a final product in powdery state.

Example 2

The process of Example 1 was repeated except that 2.5% sodium alginate aqueous solution was employed in place of 5% sodium alginate aqueous solution.

Example 3

The process of Example 1 was repeated except that 1% sodium alginate aqueous solution was employed in place of 5% sodium alginate aqueous solution.

Example 4

The process of Example 1 was repeated except that the aqueous solution mixture of 20 parts of 5% sodium alginate aqueous solution and 5 parts of 5% polyamino acid aqueous solution was employed in place of 5% sodium alginate aqueous solution.

Example 5 to 7

The process of Example 1 was repeated except that the aqueous solution mixtures of 20 parts of 5% sodium alginate aqueous solution and 5 parts of 5% hydroxypropyl methylcellulose (or polyacrylic acid[, or collagen) aqueous solution were employed in place of 5% sodium alginate aqueous solution.

Example 8

The process of Example 1 was repeated except that sodium salicylate was employed as a model drug in place of 5-fluorouracil.

Example 9

The process of Example 1 was repeated except that Omeprazole, which degrades rapidly in the strong acidic condition of gastric juice, was employed as a model drug in place of 5-fluorouracil.

In this case, the microencapsulated emulsion was obtained as a bead form (the aggregate of powdery microencapsulated emulsion) and the enteric-coated bead with hydroxypropyl methylcellulose phthalate as a capsule material for enteric coating was used as a drug carrier for Omeprazole.

Example 10 to 12

The process of Example 1 was repeated except that 5% pectin, CMC, and XCPS aqueous solution was employed in place of 5% sodium alginate aqueous solution.

Comparative example 1

The process of Example 1 was repeated except that water was employed in place of 5% sodium alginate aqueous solution.

Comparative example 2

The process of comparative Example 1 was repeated except that sodium salicylate was employed as a model drug in place of 5-fluorouracil.

In Table 1, the release pattern of drugs (5-fluorouracil and sodium salicylate) from the drug carrier system is presented.

The drug carrier systems using the microencapsulated emulsion or emulsion was prepared according to the process described in Examples 1, 8, 10, 11, 12, and Comparative Examples 1, 2. The drug release experiment was performed in artificial gastric juice (pH=2) using a dialysis bag.

TABLE 1

Drug release pattern in the strong acidic condition (pH = 2) of artificial gastric juice.

| Example No. | Amount of released drug (mg) | |
|---|---|---|
| | after 3 hours | after 24 hours |
| Example 1 | 2.01 | 9.50 |
| Example 8 | 8.10 | 22.8 |
| Example 10 | 3.52 | 12.42 |
| Example 11 | 4.12 | 14.10 |
| Example 12 | 3.77 | 12.94 |
| Comp. example 1 | 13.5 | 50.3 |
| Comp. example 2 | 30.5 | 100.1 |

The amount of drug released from the drug carrier system was measured at 3 and 24 hours.

The results show that the amount of drug released from the microencapsulated emulsion during the first 3 hours is much less than that from emulsion without capsule material (control) indicating that the drug carrier system is this invention can repress the drug release in the strong acidic condition of gastric juice.

In addition, it was confirmed by a microscope that the stability of the microencapsulated emulsions in the strong acidic condition of gastric juice was improved significantly in comparison with that of the control.

That is, it was observed that the microencapsulated emulsion prepared according to example 1 stayed intact in artificial gastric juice during the 24 hour period, while the emulsion prepared according to comparative Example 1 was disintegrated and aggregated during 30 minutes in artificial gastric juice.

FIG. 1 shows the drug release pattern in the artificial gastric juice as a function of the concentration of capsule material. The amount of drug released from the drug carrier system decreases as the concentration of sodium alginate solution used as capsule material increases. This is further evidence that the drug release is hindered by the capsule wall of the microencapsulated emulsion.

TABLE 2

The stability of drug carrier system in the artificial gastric juice and the release pattern of Omeprazole in the artificial intestinal fluid.

| | |
|---|---|
| Amount of drug carrier system used in each experiment | 100 mg |
| Loading amount | 20 mg |
| Amount of Omeprazole after staying in the artificial gastric juice for 2 hours (37° C.) | 18.5 mg |
| Amount of released Omeprazole in the artificial intestinal fluid within 10 minute (37° C.) | 19 mg |

*All the experiments were performed according to the procedures presented in U.S.P.

In Table 2, the stability of Omeprazole in the drug carrier system and the release pattern of the Omeprazole from the drug carrier system were observed using the microencapsulated emulsion as a drug carrier system. The drug carrier system was prepared according to the process described in Example 9 and the model drug was Omeprazole which degraded rapidly in the gastric juice. More than 90% of total loading amount of Omeprazole remained stable after the stay in the artificial gastric juice (37° C.) for 2 hours.

This drug carrier system was disintegrated rapidly in the artificial intestinal fluid and more than 90% of Omeprazole in the drug carrier system was released within 10 minutes.

Thus the microencapsulated emulsion in this invention can be used effectively as the drug carrier system for an oral drug which is unstable in the gastric juice.

As is apparent from the above results, the present invention provides a controlled oral drug carrier system which minimizes the degradation of drug in the gastrointestinal tract and maximizes the absorption of drug in the small intestine.

What is claimed is:

1. A microencapsulated emulsion comprising a drug-dispersed oil core, the oil core comprising a drug incorporated into a liquid oil in an amount of approximately 1–40% by weight of the oil, the oil core being surrounded by a water-insoluble capsule material present in an amount of approximately 100–200% by weight of the total weight of the oil core, said capsule material comprising a polysaccharide which has metal chelating capacity, a biocompatible and water-soluble polymer for improving the physical properties of the capsule material, said polymer being chosen from the group consisting of hydroxypropyl methylcellulose, water-soluble polyamino acid, the sodium salt of polyacrylic acid and collagen; and emulsifying agents in an amount of approximately 5–10% by weight of the total amount of the capsule material and oil core, the droplet size of the microencapsulated emulsion being approximately 1–5µm, the weight ratio of polysaccharide to polymer in the capsule material being at least 0.25.

2. The emulsion of claim 1, wherein the polysaccharide is present at between approximately 2.5 and 5% by weight of the capsule material.

3. The emulsion of claim 1, wherein the polysaccharide is chosen from the group consisting of sodium alginate, pectin, xanthomonas campestrix and carboxymethyl cellulose.

4. The emulsion of claim 2, wherein the polysaccharide is chosen from the group consisting of sodium alginate, pectin, xanthomonas campestrix and carboxymethyl cellulose.

5. The emulsion of claim 1, wherein the oil phase is an edible oil chosen from the group consisting of corn oil, peanut oil, coconut oil, castor oil, sesame oil, soybean oil, perilla oil, sunflower oil and walnut oil.

6. The emulsion of claim 2, wherein the oil phase is an edible oil chosen from the group consisting of corn oil, peanut oil, coconut oil, castor oil, sesame oil, soybean oil, perilla oil, sunflower oil and walnut oil.

7. The emulsion of claim 1, wherein the emulsifying agent is a biocompatible emulsifying agent chosen from the group consisting of Tween 20, Tween 40, Tween 80, sodium cholate, bile salt, a mixture of 80 w/v % polyethylene glycol 1000 mono cetyl ether and 20 w/v % polyethylene glycol 400, and polyoxyethylene ether.

8. The emulsion of claim 2, wherein the emulsifying agent is a biocompatible emulsifying agent chosen from the group consisting of Tween 20, Tween 40, Tween 80, sodium cholate, bile salt, a mixture of 80 w/v % polyethylene glycol 1000 mono cetyl ether and 20 w/v % polyethylene glycol 400, and polyoxyethylene ether.

9. The emulsion of claim 1, wherein the multivalent cation is chosen from the group consisting of aluminum ion, calcium ion, and magnesium ion.

10. The emulsion of claim 2, wherein the multivalent cation is chosen from the group consisting of aluminum ion, calcium ion, and magnesium ion.

11. The emulsion of claim 1, wherein the drug is stable under subjection to sonication, and is chosen from the group consisting of asteroid drug, an antibiotic, an antitumor drug, and an antiulcer drug which degrades rapidly in strong acidic conditions.

12. The emulsion of claim 2, wherein the drug is stable under subjection to sonication, and is chosen from the group consisting of a steroid drug, an antibiotic, an antitumor drug, and an antiulcer drug which degrades rapidly in strong acidic conditions.

13. The emulsion of claim 11, wherein the antiulcer drug is Omeprazole.

14. The emulsion of claim 12, wherein the antiulcer drug is Omeprazole.

* * * * *